US010065914B1

(12) United States Patent
Ruhl et al.

(10) Patent No.: US 10,065,914 B1
(45) Date of Patent: Sep. 4, 2018

(54) THERMOLYSIS OF POLYPROPIOLACTONE TO PRODUCE ACRYLIC ACID

(71) Applicant: Novomer, Inc., Waltham, MA (US)

(72) Inventors: John Ruhl, Rochester, NY (US); Kyle Evan Sherry, Rochester, NY (US)

(73) Assignee: Novomer, Inc., Boston, MA (US)

( * ) Notice: Subject to any disclaimer, the term of this patent is extended or adjusted under 35 U.S.C. 154(b) by 0 days.

(21) Appl. No.: 15/494,805

(22) Filed: Apr. 24, 2017

(51) Int. Cl.
*C07C 51/377* (2006.01)
*B01J 19/18* (2006.01)
*B01J 19/24* (2006.01)
*B01J 19/00* (2006.01)

(52) U.S. Cl.
CPC ......... *C07C 51/377* (2013.01); *B01J 19/0066* (2013.01); *B01J 19/18* (2013.01); *B01J 19/2405* (2013.01); *B01J 2219/00051* (2013.01); *B01J 2219/24* (2013.01)

(58) Field of Classification Search
CPC .................................................. C07C 51/377
See application file for complete search history.

(56) References Cited

U.S. PATENT DOCUMENTS

| | | | | |
|---|---|---|---|---|
| 2,361,036 | A | * | 10/1944 | Kung .................... C07C 51/347 528/355 |
| 3,002,017 | A | | 9/1961 | Wearsch |
| 3,169,945 | A | | 2/1965 | Fritz et al. |
| 3,678,069 | A | | 7/1972 | Busler |
| 3,954,854 | A | * | 5/1976 | Gehrmann et al. ... C07C 51/487 562/599 |
| 4,317,926 | A | | 3/1982 | Sato et al. |
| 4,792,620 | A | * | 12/1988 | Paulik ................... B01J 31/0231 560/232 |
| 5,310,948 | A | | 5/1994 | Drent et al. |
| 5,359,081 | A | | 10/1994 | Drent et al. |
| 5,648,452 | A | | 7/1997 | Schechtman |
| 6,133,402 | A | | 10/2000 | Coates et al. |
| 6,252,110 | B1 | | 6/2001 | Uemura et al. |
| 6,316,590 | B1 | | 11/2001 | Coates et al. |
| 6,538,101 | B2 | | 3/2003 | Coates et al. |
| 6,608,170 | B1 | | 8/2003 | Coates |
| 6,852,865 | B2 | | 2/2005 | Coates et al. |
| 6,887,380 | B2 | | 5/2005 | Lee et al. |
| 7,420,064 | B2 | | 9/2008 | Luinstra et al. |
| 9,115,070 | B2 | | 8/2015 | Pazicky et al. |
| 2005/0014977 | A1 | | 1/2005 | Drent et al. |
| 2007/0161806 | A1 | | 7/2007 | Preishuber-Pflugl et al. |
| 2014/0018574 | A1 | | 1/2014 | Raith et al. |
| 2014/0275575 | A1 | | 9/2014 | Allen et al. |
| 2015/0183708 | A1 | | 7/2015 | Harris et al. |
| 2017/0029352 | A1 | * | 2/2017 | Sookraj .................... C07C 51/09 |

FOREIGN PATENT DOCUMENTS

| | | |
|---|---|---|
| EP | 0577206 | 1/1994 |
| EP | 0 887 334 B1 | 12/1998 |
| WO | WO 2011/100608 A1 | 8/2011 |
| WO | 2011163309 | 12/2011 |
| WO | 2013063191 | 5/2013 |
| WO | WO 2013/063191 A1 | 5/2013 |
| WO | 2013126375 | 8/2013 |
| WO | WO 2013/126375 A1 | 8/2013 |
| WO | WO 2013/185009 A1 | 12/2013 |
| WO | 2014008232 | 1/2014 |
| WO | WO 2014/004858 A1 | 1/2014 |
| WO | WO 2014/008232 A2 | 1/2014 |
| WO | WO 2017/023777 A9 | 2/2017 |
| WO | WO 2017/023820 | 2/2017 |
| WO | 2018085254 | 5/2018 |

OTHER PUBLICATIONS

Norskov et al, Nature Chemistry, Towards the Computational Design of Solid Catalysts, 2009, 1, pp. 37-46 (Year: 2009).*
Iwabuchi, Susumu, et al. "The Thermal Degradation of Poly(oxycarbonylethylene) (Poly-beta-propiolactone)" from Die Makromolekulare Chemie (1973) at pp. 59-72.
Notification of Transmittal of the International Search Report and Written Opinion dated Nov. 8, 2016, issued in International Application No. PCT/US2016/044772 (19 pages).
Notification of Transmittal of the International Search Report and Written Opinion dated Nov. 8, 2016, issued in International Application No. PCT/US2016/044927 (19 pages).
Sorrell, Thomas. Organic Chemistry, University Science Books, Sausalito, 1999.
Liu et al. Reducing the Formation of Six-Membered Ring Ester During Thermal Degradation of Biodegradable PHBV to Enhance its Thermal Stability. Polymer Degradation and Stability, 94 (2009) pp. 18-24.
Beta Elimination of Esters in Poly Lactones, Aug. 17, 2017.
Nguyen et al. Thermal Degradation of Poly(3-hydroxyalkanoates): Preparation of Well-Defined Oligomers. Biomacromolecules, 3 (2002) pp. 219-224.
JP 45-19281 Recovery of AA from dimer (Rus) (1). (Machine English translation attached.).

(Continued)

*Primary Examiner* — Paul A Zucker
(74) *Attorney, Agent, or Firm* — Beem Patent Law Firm; Justin Cain

(57) ABSTRACT

The present invention is directed to reactor apparatus and processes for thermolysis of polypropiolactone to produce highly pure acrylic acid. In preferred embodiments of the present invention, the processes comprise introducing a feed stream comprising polypropiolactone to a thermolysis process vessel through an inlet; maintaining a concentration of active salt by adding and removing portions of active salt by at least one inlet and at least one outlet; heating the thermolysis process vessel; and recovering a product including acrylic acid from an outlet. In certain preferred embodiments, the active salt may be present as a catalyst used for polymerization of the polypropiolactone in the feed stream. In some embodiments, one or more active salts may be added to the feed stream and/or the thermolysis process vessel.

13 Claims, 7 Drawing Sheets

(56) References Cited

OTHER PUBLICATIONS

Kim et al. Effect of Metal Compounds on Thermal Degradation Behavior of Aliphatic Poly(hydroxyalkanoic acid)s. Polymer Degradation and Stability, 93 (2008) pp. 776-785.
Kim et al. Effects of Residual Metal Compounds and Chain-End Structure on Thermal Degradation of Poly(3-hydroxybutyric acid). Polymer Degradation and Stability, 91 (2006) pp. 769-777.
Zhu et al. Polymorphic Crystallization and Melting-Recrystallization Behavior of Poly(3-hydroxypropionate). Macromolecules, 38 (2005) pp. 6455-6465.
Kim et al. Thermal Degradation Behavior of Poly(4-hydroxybutyric acid). Polymer Degradation and Stability, 91 (2006) pp. 2333-2341.
Varma-Nair et al. Heat Capacity and Other Thermodynamic Properties of Linear Macromolecules (1980).
Kopinke et al. Thermal Decomposition of Biodegradable Polyesters—I: Poly(beta-hydroxybutyric acid). Polymer Degradation and Stability, 52 (1996) pp. 25-38.
Abe. Thermal Degradation of Environmentally Degradable Poly(hydroxyalkanoic acid)s. Macromolecular Bioscience (2006) pp. 469-486.
Abe et al. Effects of Residual Zinc Compounds and Chain-End Structure on Thermal Degradation of Poly(epsilon-Caprolactone). Biomacromolecules, 5 (2004) pp. 1480-1488.
Dunn. Synthesis of Poly(hydroxyalkanoates): Routes to Poly(3-hydroxybutyrate) and Poly(3-hydroxypropionate) from the Carbonylation and Ring-Opening Polymerization of Epoxides. Dissertation, Cornell University (2012).
Jacobi et al. Strukturuntersuchung von Polyestern durch direkten Abbau im Massenspektrometer, 4. Makromol. Chem., 179 (1978) pp. 429-436.
Kricheldorf et al. Strukturuntersuchung von Polyestern durch direkten Abbau im Massenspektrometer, 3. Makromol. Chem., 179 (1978) pp. 421-427.
Garozzo et al. Primary Thermal Decomposition Processes in Aliphatic Polyesters Investigated by Chemical Ionization Mass Spectrometry. Macromolecules, 19 (1986) pp. 1643-1649.
Gresham et al. Beta-Propiolactone I. Polymerization Reactions. vol. 70 (1948) pp. 998-999.
Gresham et al. Beta-Propiolactone II. Reactions with Salts of Inorganic Acids. vol. 70 (1948) pp. 999-1001.
Gresham et al. Beta-Propiolactone III. Reactions with Dithiocarbamic Acids, their Salts and Thiourea. vol. 70 (1948) pp. 1001-1002.
Gresham et al. Beta-Propiolactone IV. Reactions with Salts of Carboxylic Acids. vol. 70 (1948) pp. 1003-1004.
Gresham et al. Beta-Propiolactone V. Reaction with Alcohols. vol. 70 (1948) pp. 1004-1006.
Luderwald et al. Strukturuntersuchung von Polyestern durch direkten Abbau im Massenspektrometer, 2. Makromol. Chem., 177 (1976) pp. 2093-2111.
Notification of Transmittal of the International Search Report and Written Opinion dated Jun. 21, 2018, issued in International Application No. PCT/US2018/029067 (16 pages).
Notification of Transmittal of the International Search Report and Written Opinion dated Jul. 6, 2018, issued in International Application No. PCT/US2018/029060 (14 pages).

\* cited by examiner

THERMOLYSIS OF POLYPROPIOLACTONE TO PRODUCE ACRYLIC ACID

FIELD OF THE INVENTION

This invention generally relates to reactor apparatus and processes for producing acrylic acid. Specifically, the reactor apparatus and processes provide high-purity acrylic acid through thermolysis of polypropiolactone. Advantageously, preferred embodiments of the present invention provide for a more efficient use of raw materials by catalyzing thermolysis of polypropiolactone with active salts in a highly efficient reactor apparatus for producing and recovering a high purity acrylic acid product stream.

BACKGROUND OF THE INVENTION

Polypropiolactone, termed "PPL" for the purposes of this application, is a biodegradable polymer that can be useful material in many manufacturing and industrial applications. The physical and chemical characteristics of PPL provide for safer transportation and storage over extended periods of time with decreased quality concerns. PPL is also a useful precursor because the polymer may undergo a chemical process known as thermolysis to produce acrylic acid.

Generally, thermolysis is a chemical decomposition reaction caused by heat. Thermolysis of PPL may proceed by two known reaction mechanisms. A first reaction mechanism, known as unzipping, includes a PPL polymer with a chain length equal to (n) that decomposes into a PPL polymer with a chain length (n−1) and a molecule of acrylic acid. The second reaction mechanism, known as internal chain scission, includes a PPL polymer with a chain length (n) decomposes into a PPL polymer with a chain length (n−x) and a PPL polymer with a chain length (x), where (x) is greater than or equal to 2.

Under certain reaction conditions, acrylic acid may be susceptible to auto-polymerization. In one auto-polymerization reaction, a first molecule of acrylic acid is added to a second molecule of acrylic acid to form a di-acrylic acid ester, which is identical to a PPL polymer with a chain length of 2. There is no known inhibitor which will prevent the addition of one molecule of acrylic acid to another. However, the di-acrylic acid ester may readily undergo thermolysis and decompose back into two molecules of acrylic acid. In a second auto-polymerization reaction, multiple molecules of acrylic acid undergo free radical polymerization to form chains of polyacrylate. These larger chains of polyacrylic acid cannot convert back into individual molecules of acrylic acid under thermolysis conditions.

Radical polymerization of acrylic acid may be limited with the use of certain known inhibitors. However, these radical polymerization inhibitors may be costly, inefficient, and/or difficult to source. Additionally, conventional thermolysis reactors may not efficiently utilize reactants or may not allow for ready recovery of acrylic acid vapor effluent. There exists a need for improved apparatus and methods for thermolyzing PPL by catalyzing thermolysis while reducing and/or limiting formation of polyacrylic acid with less expensive, more efficient, and more easily sourced materials. The present invention satisfies this need by providing reactor apparatus and processes for thermolysis of PPL which may be configured to maintain concentrations of active salt.

SUMMARY OF THE INVENTION

There exists a need for innovative reactor apparatus and processes by which higher purity acrylic acid may be produced from PPL by reducing the amount of acrylic acid product that is polymerized during a thermolysis reaction. Preferred embodiments of the present invention may reduce and/or limit the polymerization of acrylic acid by catalyzing the thermolysis of PPL with one or more active salt. Advantageously, the one or more active salt may reduce certain thermolysis reaction conditions such as temperature and/or time. Reduced thermolysis reaction conditions may provide for a thermolysis reaction that proceeds at a higher rate relative to radical polymerization of acrylic acid. In certain preferred embodiments, a highly efficient reactor may be configured to remove acrylic acid product and reduce acrylic acid available for polymerization.

In one aspect, the present invention provides a solution to the problems inherent in the storage and transportation of acrylic acid. In another aspect, the present invention enables a less expensive feedstock to be used for acrylic acid production. In one other aspect, the present invention provides for increased efficiency when using feedstock on site to satisfy broader geographic demand for acrylic acid and its derivatives. Aspects of the present invention overcome the deficiencies of conventional systems by incorporation of components allowing for continuous flow and separation of products as a vapor effluent.

Provided herein are apparatus and processes for producing high purity acrylic acid by catalyzing a thermolysis reaction of PPL relative to radical polymerization of acrylic acid with concentrations of active salt.

In preferred embodiments of the present invention, the processes comprise providing a feed stream including PPL. The feed stream may comprise PPL as a liquid and/or solid and the PPL may have a varying chain length. In certain preferred embodiments, the PPL preferably may be present in the feed stream at a high concentration by weight. In some embodiments, the feed stream may also include beta-propiolactone and/or sodium acrylate. Beta-propiolactone ("bPL") preferably may be present in the feed stream at a lower concentration by weight. An active salt preferably may be present in the feed stream at a lower concentration by weight. Phenothiazine may be present with the active salt for free radical polymerization inhibition.

In preferred embodiments of the present invention, the reactor apparatus includes a thermolysis process vessel configured for decomposing PPL and recovering acrylic acid under thermolysis conditions. The thermolysis process vessel comprises a decomposition chamber sized and shaped to define an interior volume adapted to receive a portion of a feed stream comprising PPL which may be introduced to the decomposition chamber by a feed stream inlet. The decomposition chamber is sized and shaped to define a retaining volume to retain a feed stream comprising PPL. The thermolysis process vessel also defines product stream outlet located on a separation chamber that is in direct communication with the decomposition chamber from which a product comprising acrylic acid may be withdrawn.

In preferred embodiments of the present invention, the reactor apparatus and processes minimize the polymerization of acrylic acid to polyacrylic acid and catalyze thermolysis of PPL. Advantageously, the loss of acrylic acid to polyacrylic acid may be reduced by maintaining a predetermined concentration of active salt to decrease the reaction rate of acrylic acid to polyacrylic acid relative to thermolysis of PPL to acrylic acid. In preferred embodiments, the active salt may be sodium acrylate, potassium acrylate, sodium carbonate, potassium carbonate, and/or tert-butyl ammonium acrylate. In certain embodiments, the processes may also minimize the loss of acrylic acid by controlling the partial pressure of acrylic acid in a vapor phase and introducing an active salt such as sodium acrylate to acrylic acid in a liquid phase.

In certain preferred embodiments, the processes may be configured for continuous PPL thermolysis with a mass flow-in approximately equal to a mass flow-out of the thermolysis process vessel. An active salt may be continually introduced to the feed stream and/or decomposition chamber for catalyzing thermolysis of polypropiolactone and diacrylic acid dimers under less severe reaction conditions. A portion of active salt may be removed from the thermolysis process vessel to prevent the decomposition chamber from reaching capacity. Advantageously, the processes configured for continuous PPL thermolysis may provide options to minimize the concentration of acrylic acid in a liquid phase which may polymerize into polyacrylic acid relative to that of PPL to acrylic acid.

In some embodiments, a separation chamber may cause portions of the feed stream in the vapor phase to undergo condensation and/or distillation to remove a product stream, higher-boiling impurities, and/or lower-boiling impurities. In some embodiments, if distillation is required to remove higher-boiling impurities, then an active salt and/or polymerization inhibitor may be introduced to liquid phase acrylic acid.

Some embodiments that use certain polymerization inhibitors may call for the management of oxygen, present as dissolved oxygen, in the decomposition chamber. These embodiments may deliver an oxygen gas or an oxygen mixed with an inert gas to the process. One example of such an embodiment includes the use of 4-methoxyphenol as a polymerization inhibitor. Other examples of polymerization inhibitors, such as phenothiazine, may not require the regulation of oxygen in the reactor system.

Preferred embodiments of the present invention may include thermolysis off PPL which was polymerized using an active salt as a catalyst. Some or all of the active salt catalyst may remain with the PPL and catalyze thermolysis of PPL to produce acrylic acid. Advantageously, a feed stream of PPL polymerized with an active salt catalyst may not need additional active salt to catalyze thermolysis.

While this disclosure is susceptible to various modifications and alternative forms, specific exemplary embodiments thereof have been shown by way of example in the drawings and have herein been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

BRIEF DESCRIPTION OF THE DRAWINGS

The present invention can be better understood by reading the following detailed description of certain preferred embodiments, reference being made to the accompanying drawings in which.

DETAILED DESCRIPTION OF EMBODIMENTS

The present invention is directed to apparatus and processes for producing higher purity acrylic acid by catalyzing thermolysis of PPL with an active salt. In certain preferred embodiments of the present invention, the active salt employed for catalyzing thermolysis may be a polymerization catalyst, such as sodium acrylate, used in a polymerization reaction for forming PPL from bPL.

Figure 1:
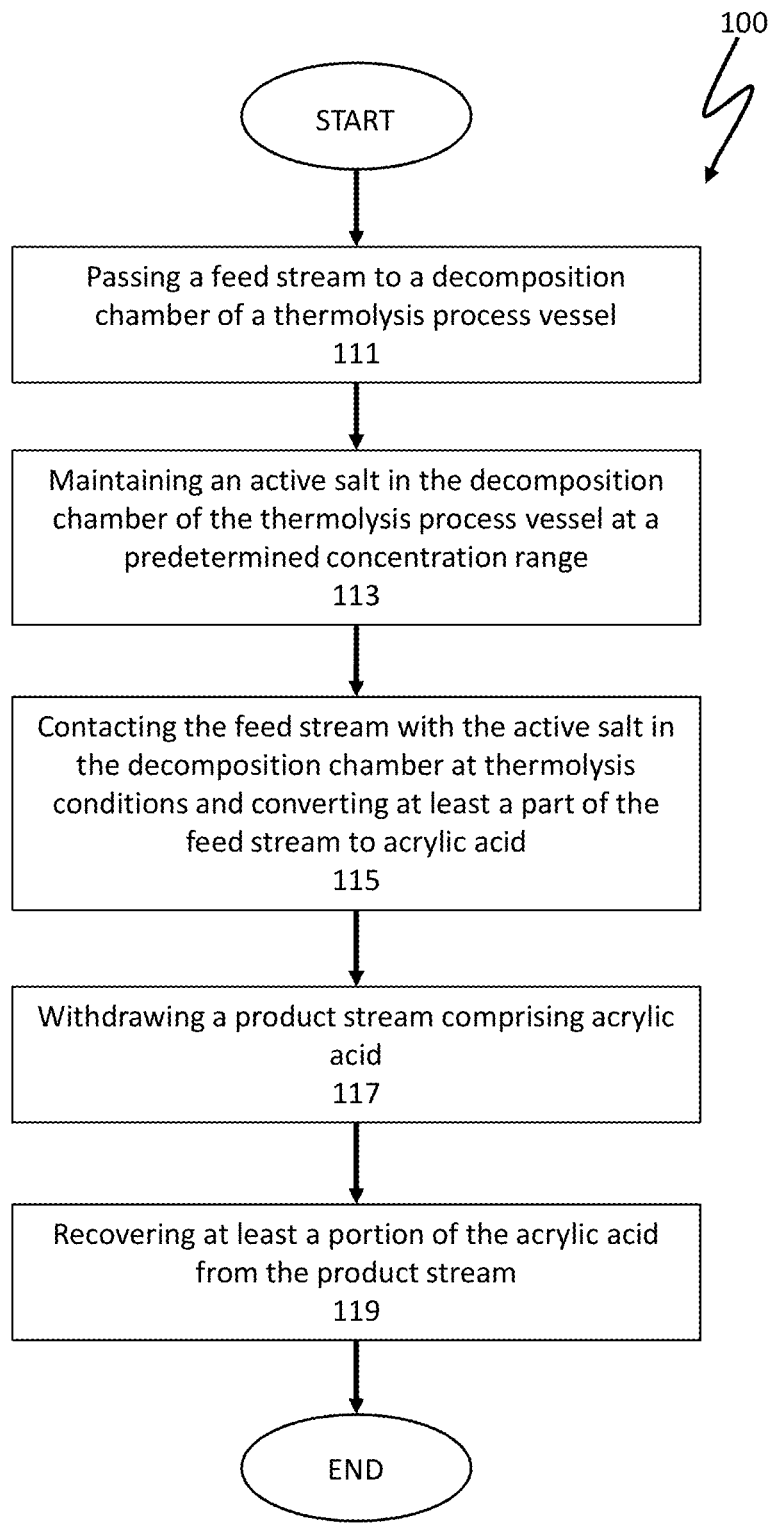
FIG. 1 illustrates steps of a preferred embodiment of a process for thermolysis of PPL to produce acrylic acid.

FIG. 1 illustrates a preferred embodiment of a process 100 for producing high purity acrylic acid. In the FIG. 1 illustrated embodiment, the process 100 comprises steps for passing a feed stream to a decomposition chamber of a thermolysis process vessel 111; maintaining an active salt in the decomposition chamber of the thermolysis process vessel at a predetermined concentration range 113; contacting the feed stream with the active salt in the decomposition chamber at thermolysis conditions an converting at least a part of the feed stream to acrylic acid 115; withdrawing a product stream comprising acrylic acid 117; and recovering at least a portion of the acrylic acid from the product stream 119.

In the FIG. 1 illustrated embodiment, passing a feed stream to a decomposition chamber of a thermolysis process vessel 111 includes a feed source comprising PPL. The PPL may be a liquid and/or solid and the PPL may have a varying chain length. In the FIG. 1 illustrated embodiment, the PPL may be present in the feed stream at a concentration between 85% and 100% by weight. The feed stream may also include bPL at a concentration between 0% and 10% by weight. An active salt may be present in the feed stream at a concentration between 0% and 10% by weight. The active salt may be residual catalyst from polymerization of bPL to PPL.

Preferred embodiments of the present invention, such as the FIG. 1 illustrated embodiment, include a step for maintaining an active salt in the decomposition chamber of the thermolysis process vessel at a predetermined concentration range 113 for catalyzing thermolysis and limiting acrylic acid available for polymerization during a thermolysis reaction. In preferred embodiments, the active salt may be sodium acrylate, potassium acrylate, sodium carbonate, potassium carbonate, and/or tert-butyl ammonium acrylate. The preferred concentration by weight of active salt for catalyzing thermolysis may be between 0.001% and 10%. In certain preferred embodiments, the preferred concentration of active salt may be between 1% and 8%. In certain other preferred embodiments, the concentration of active salt may be between 3% and 6%. In certain preferred embodiments, the active salt may be sodium acrylate.

In certain preferred embodiments, Contacting the feed stream with the active salt in the decomposition chamber at thermolysis conditions and converting at least a part of the feed stream to acrylic acid 115 includes contacting active salt with the feed stream outside of the decomposition chamber and/or inside the decomposition chamber. For example, sodium acrylate added with the feed stream may be present as an impurity from the polymerization reaction of PPL or may be added separately to the feed stream. In some embodiments, active salt may be added to the thermolysis process vessel separately such as during the thermolysis reaction and/or as needed to reduce and/or limit polymerization of acrylic acid during the thermolysis reaction. In certain preferred embodiments, the active salt catalytically cleaves acrylic acid molecules from PPL at a quicker rate than acrylic acid radically polymerizes during thermolysis.

In some embodiments, certain other polymerization inhibitors may also be added including, for example, phenothiazine and 4-methoxyphenol.

In certain preferred embodiments of the present invention, such as the FIG. 1 illustrated embodiment, the step for contacting the feed stream with the active salt in the decomposition chamber at thermolysis conditions and converting at least a part of the feed stream to acrylic acid includes thermolysis conditions that may occur between 100° C. and 320° C., and include an absolute pressure between 1 torr and 5,000 torr. A heating component may be used for maintaining a temperature of the thermolysis process vessel and may include one of many devices known to one skilled in the art, for example, internal coils, external heat exchanger with a pump-around loop, or a baffled jacket on the walls of the decomposition chamber. In some embodiments, the feed stream may have a residence time between a few seconds and 24 hours. Advantageously, a concentration range of active salt may decrease the temperature of thermolysis and/or increase the rate of thermolysis at certain temperatures.

In preferred embodiments, such as the process 100 illustrated in FIG. 1, withdrawing a product stream comprising acrylic acid 117 includes a product stream comprising acrylic acid at a concentration exceeding 85% by weight. In certain preferred embodiments, the product stream comprises acrylic acid at a concentration by weight percent exceeding 95%, preferably 98% and more preferably exceeding 99.8% by weight.

In certain embodiments, the process 100 may include steps for reducing the concentration of acrylic acid in the thermolysis process vessel's liquid contents, and therefore the likelihood of forming polyacrylic acid. For some embodiments, the presence of liquid acrylic acid may be reduced by controlling the thermolysis process vessel internal pressure. Reducing the partial pressure of acrylic acid in the thermolysis process vessel may reduce the amount of acrylic acid present in a liquid state and the likelihood of radical polymerization. In some embodiments, a continuous flow of a product stream, recycle stream, and/or purge stream may be configured to reduce the polymerization and subsequent accumulation of polyacrylic acid and any other nonvolatile components. In some embodiments, the recycle stream may be directed to a secondary thermolysis process vessel or be recycled and directed to the original thermolysis process vessel.

Figure 2:
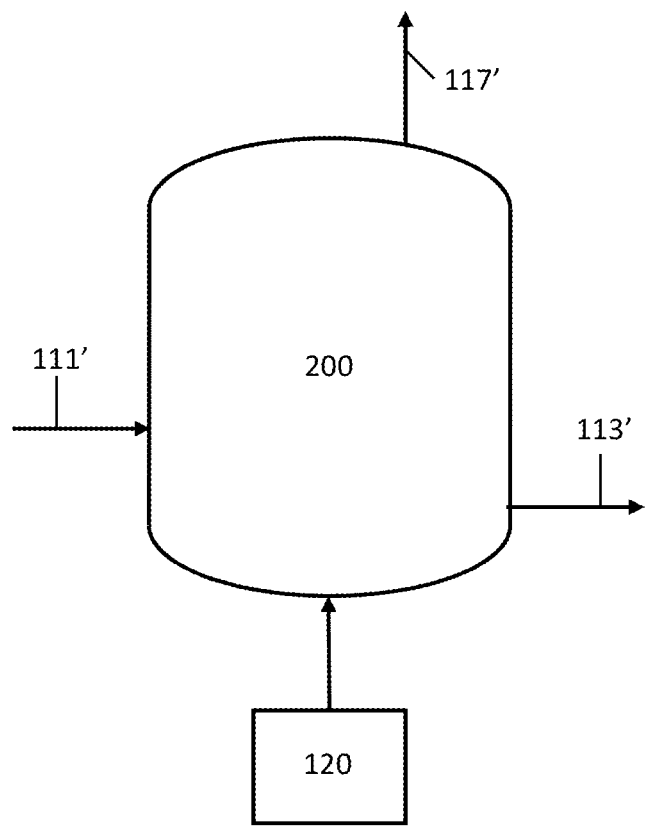
FIG. 2 is a schematic process flow diagram illustrating steps of the process flow from FIG. 1.

FIG. 2 provides a schematic view diagram of some of the process steps of FIG. 1. The process flow of FIG. 2 is configured for continuous thermolysis of PPL using a thermolysis process vessel 200 to which a feed stream 111' comprising PPL and an active salt passes in accordance with step 111 of FIG. 1. A line 113' removes a portion of material from the thermolysis process vessel 200 to maintain a desired concentration range of active salt in the thermolysis process vessel in accordance with step 113 of FIG. 1. Withdrawal of liquid by line 113' removes a portion of active salt from the thermolysis process vessel 200 along with other contents of the thermolysis process vessel 200 which may be recycled back to the thermolysis process vessel 200 after removal of at least a portion of the active salt.

The process will include a heat source 120 for maintaining the temperature of the thermolysis process vessel 200 at the necessary temperature and provide heat for thermolysis reaction. FIG. 2 shows an external heat source 120 transferring heat to the thermolysis process vessel 200. Alternatively, the heat source 120 may directly generate heat within the thermolysis process vessel 200. A line 117' withdraws a product stream comprising acrylic acid from the thermolysis process vessel 200 in accordance with step 117 of FIG. 1.

Figure 3:
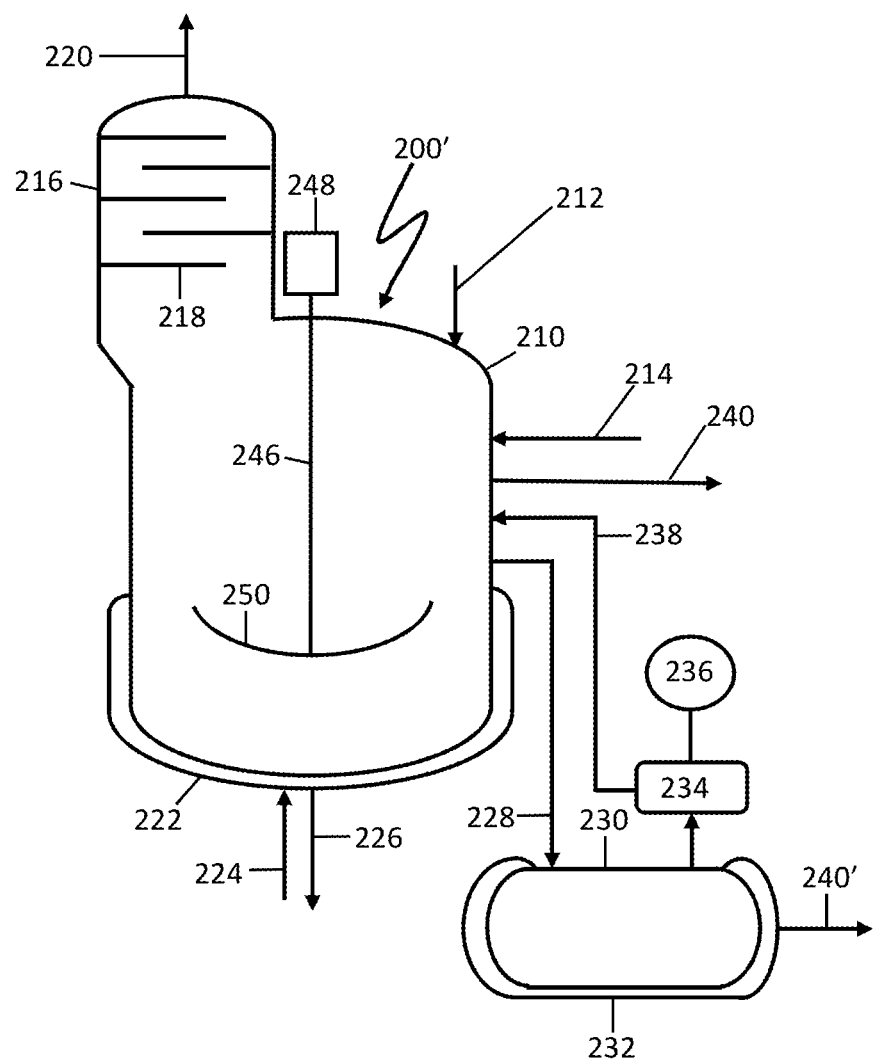
FIG. 3 schematically illustrates a preferred reactor apparatus and related equipment in a process flow diagram for thermolysis of PPL to produce acrylic acid.

FIG. 3 illustrates a preferred embodiment of a thermolysis process vessel 200' configured for decomposing PPL and recovering acrylic acid. In the FIG. 3 illustrated embodiment, the thermolysis process vessel 200' defines a decomposition chamber 210 sized and shaped to define interior volume adapted for receiving a feed stream comprising PPL and a retaining volume adapted for retaining a feed stream comprising PPL. The feed stream comprising PPL may be passed to the decomposition chamber 210 by a feed stream inlet 212 defined by the decomposition chamber 210. In some embodiments, an active salt may be directly introduced to the decomposition chamber 210 by an additive stream inlet 214 defined by a portion of the decomposition chamber 210. Additionally, oligomers of a variety of chain lengths, di-acrylic acid, residual bPL polymerization initiator, radical polymerization inhibitor, acrylic acid, and/or radically polymerized acrylic acid of a variety of chain lengths may be removed directly from the decomposition chamber 210 by a purge stream outlet 240 defined by the decomposition chamber 210.

In certain preferred embodiments of the present invention, the apparatus includes a thermolysis process vessel 200' defining a separation chamber 216 configured for direct communication with an upper portion of the decomposition chamber 210. The separation chamber 216 may comprise a fractioning and/or rectification column having one or more trays 218. A product stream comprising acrylic acid is withdrawn by a product stream line 220 through an outlet defined by an upper section of the separation chamber 216. A portion of product stream may be cooled and returned to the one or more trays 218 of the separation chamber 216. A condensate may flow out of the bottom of the separation chamber 216 and return a mixture of acrylic acid, di-acrylic acid, and short-chain PPL oligomers to the decomposition chamber 210 for thermolysis. The product stream comprising acrylic acid may undergo cooling and further processing. The processing may include additional purification to remove by-products, unrelated feed components and other impurities.

The thermolysis process vessel 200' also includes a heater 222 to provide heat for endothermic conversion of the PPL to acrylic acid. FIG. 3 shows a heater 222 in the form of a heating jacket that surrounds a lower portion of the decomposition chamber 210. In alternate embodiments, the heater 222 may be an external heat exchanger connected to the decomposition chamber 210 with a pump-around loop for circulation of hot fluid. In the embodiment of FIG. 3 a hot fluid stream influent line 224 delivers hot fluid to the heater 222 and a hot fluid stream effluent line 226 removes hot fluid from the heater 222. Suitable fluids include hot oil and molten salts.

In certain preferred embodiments, the thermolysis process vessel 200' may define a slip stream outlet 228 which may direct PPL polymer and PPL oligomers of a variety of chain lengths, di-acrylic acid, residual bPL polymerization initiator, radical polymerization inhibitor, acrylic acid, and/or radically polymerized acrylic acid of a variety of chain lengths to a bottoms squeezer 230. The bottoms squeezer 230 is a reactive distillation vessel such as a thin film evaporator for thermolysis of PPL polymer and PPL oligomers into volatile species like acrylic acid, di-acrylic acid, and PPL oligomers of a variety of chain lengths. The bottoms squeezer 230 is connected to a bottoms squeezer heater 232 for heating the contents of the bottoms squeezer 230. The volatile species are withdrawn from the bottoms squeezer 230 through a bottoms squeezer condenser 234 by a vacuum source 236 and returned to the decomposition chamber 210 or mixed with the product stream 220. The volatile species like acrylic acid and di-acrylic acid are returned to the decomposition chamber 210 by a recycle stream inlet 238. The liquid residence time in the bottoms squeezer 230 may be between 5 seconds and 3 hours, depending upon flow conditions and operating temperature, but is preferably 10-30 minutes. Less volatile and non-decomposable species such as residual bPL polymerization initiator, radical polymerization inhibitor, and radically polymerized polyacrylic acid are removed from the bottoms squeezer by a purge stream line 240'. Additionally, oligomers of a variety of chain lengths, di-acrylic acid, residual bPL polymerization initiator, radical polymerization inhibitor, acrylic acid, and/or radically polymerized acrylic acid of a variety of chain lengths may be removed directly from the decomposition chamber 210 by a purge stream line 240'.

The thermolysis process vessel 200' illustrated in FIG. 3 is configured to included mechanical mixing. A mechanical mixer 246 may be rotated by a motor 248 so that at least one blade 250 provides mechanical mixing to the material in the retaining volume of the decomposition chamber 210.

Figure 4:
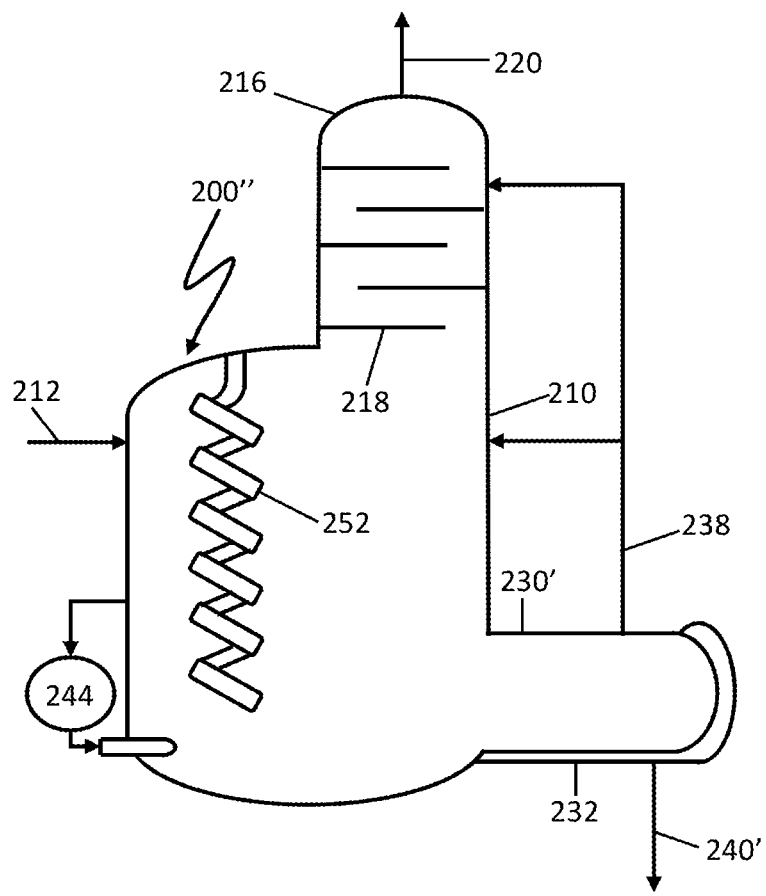
FIG. 4 illustrates another preferred embodiment including a thermolysis process vessel for thermolysis of PPL to produce acrylic acid.

FIG. 4 illustrates another preferred embodiment of a thermolysis process vessel 200" configured for continuous flow. The thermolysis process vessel 200" includes a decomposition chamber 210 sized and shaped to define a feed stream inlet 212 for receiving a feed stream comprising PPL. The decomposition chamber 210 is in direct communication with a separation chamber 216 connected to a product stream line 220 at the top of the separation chamber 216. The separation chamber 216 is a rectification column with one or more trays 218. In FIG. 4, a heating coil 252 has heat exchange tubes through which hot liquid or gas may be circulated for providing heat internally to the feed stream. The retaining volume of the decomposition chamber 210 is also in direct communication with a bottoms squeezer 230' so that PPL polymer and PPL oligomers of a variety of chain lengths, di-acrylic acid, residual bPL polymerization initiator, radical polymerization inhibitor, acrylic acid, and/or radically polymerized acrylic acid of a variety of chain lengths may be heated under thermolysis conditions. The bottoms squeezer 230' is connected to a bottoms squeezer heater 232 for thermolyzing small chain PPL oligomers and distilling acrylic acid to be returned to the separation chamber 216 by a recycle stream inlet 238. Less volatile materials such as residual bPL polymerization initiator, radical polymerization inhibitor, and/or radically polymerized acrylic acid of a variety of chain lengths may be removed by a purge stream line 240'. The contents of the decomposition chamber 210 are mixed by a jet mixer 244 which may remove liquid from the retaining volume of the decomposition chamber 210 and return the liquid to the retaining volume of the decomposition chamber 210 such as with a pump.

In certain embodiments, such as the embodiment illustrated in FIG. 4, it may be preferable to withdraw the product stream comprising acrylic acid in a vapor phase. The separation chamber 216 illustrated in FIG. 4 may cause the feed stream in vapor phase to undergo condensation and/or distillation to remove higher-boiling and/or lower-boiling impurities. In some embodiments, if distillation is required to remove higher-boiling impurities, then active salt and/or polymerization inhibitor may be introduced to any liquid phase acrylic acid, for example, in the decomposition chamber 210 and/or the separation chamber 216. In some embodiments, if 4-methoxyphenol is used as a polymerization inhibitor, the concentration of dissolved oxygen may be managed oxygen gas or oxygen mixed with an inert gas may be delivered to the decomposition chamber. The bottom portions from the separation chamber 216 shall optimally be returned to the decomposition chamber 210 for further thermolysis. In some embodiments, the separation chamber 216 may reduce the partial pressure of acrylic acid and the concentration acrylic acid in the process vessel's liquid contents. In another example, said vapors may be expelled from the product stream outlet when the partial pressure of acrylic acid is above a defined amount.

In some embodiments, such as the FIG. 4 illustrated embodiment, the bottoms squeezer 230' may be a reactive distillation vessel, such as a thin film evaporator either oriented vertically or horizontally, or a continuous agitated-tank reactor followed by a condenser (not shown in FIG. 4). The bottoms squeezer 230' may be operated at a temperature preferably in excess of 100° C., but may also be heated along its length to a higher temperature, cooled immediately to a lower temperature, and/or cooled along the length of the bottoms squeezer 230' to a lower temperature. The bottoms squeezer 230' may generally be operated below atmospheric pressure. The liquid residence time in the bottoms squeezer may be between 30 seconds and 30 hours, depending upon feed conditions and operating temperature, but preferably 2-15 minutes.

Figure 5:
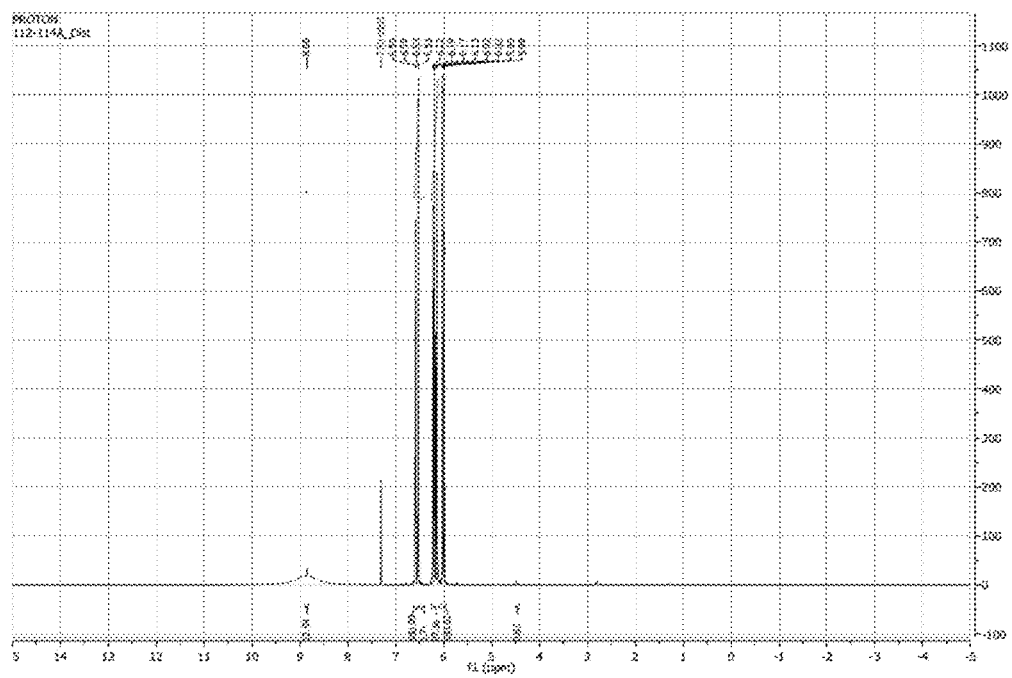
FIG. 5 illustrates a H NMR graph of a product stream from a preferred embodiment maintaining a concentration of active salt between 0.001% and 1% by weight.

FIG. 5 illustrates the hydrogen nuclear magnetic resonance ("H NMR") graph of an acrylic acid product stream from an embodiment of the present invention wherein the process included maintaining a concentration range of sodium acrylate between 0.001% and 1% by weight in the thermolysis process vessel.

The acrylic acid product represented by the FIG. 5 illustration is produced using a lab-scale batch thermolysis process vessel comprising a two-necked round-bottom glass flask of 25 mL approximate internal volume. The thermolysis process vessel is equipped with an internal thermocouple and the top center opening is equipped with a separation chamber comprising a Vigreux column oriented coaxially (similar to Ace Glass item #6578-04), followed by an adapter with an additional thermocouple to monitor vapor temperature, followed by a water-cooled condenser, and finally a four-armed product receiver in a dry ice/acetone-cooled dewar. The thermolysis process vessel includes a heater comprising a fabric heating mantle, the power to which is controlled by a temperature controller that receives feedback from the thermocouple inside the thermolysis process vessel. The thermolysis process vessel includes a stirrer comprising a magnetic stir plate and a PTFE-coated stir bar.

The feed stream introduced to the thermolysis process vessel is comprised of 5 mg phenothiazine and 6.660 g of PPL produced from ring-opening polymerization of solvent-free bPL in the presence of sodium acrylate at a concentration of 1 mol per 6,000 mol of bPL and phenothiazine at a concentration of 200 ppmw in bPL. The feed stream is heated in the thermolysis process vessel to 90° C. to melt and begin stirring. The thermolysis process vessel is brought under vacuum to an absolute pressure of approximately 400 torr, and the thermolysis process vessel temperature setpoint was set to 230° C. Internal reflux was observed inside the reaction flask within minutes.

The product sample 112-114A_Dist had a mass of 0.516 g, of a total 5.667 g total distillate collected. The HNMR analysis suggests an average acrylic acid content in 112-114A_Dist of 99.2%. The balance consists of di-acrylic acid ester and traces of other PPL oligomers where n>2.

Figure 6:
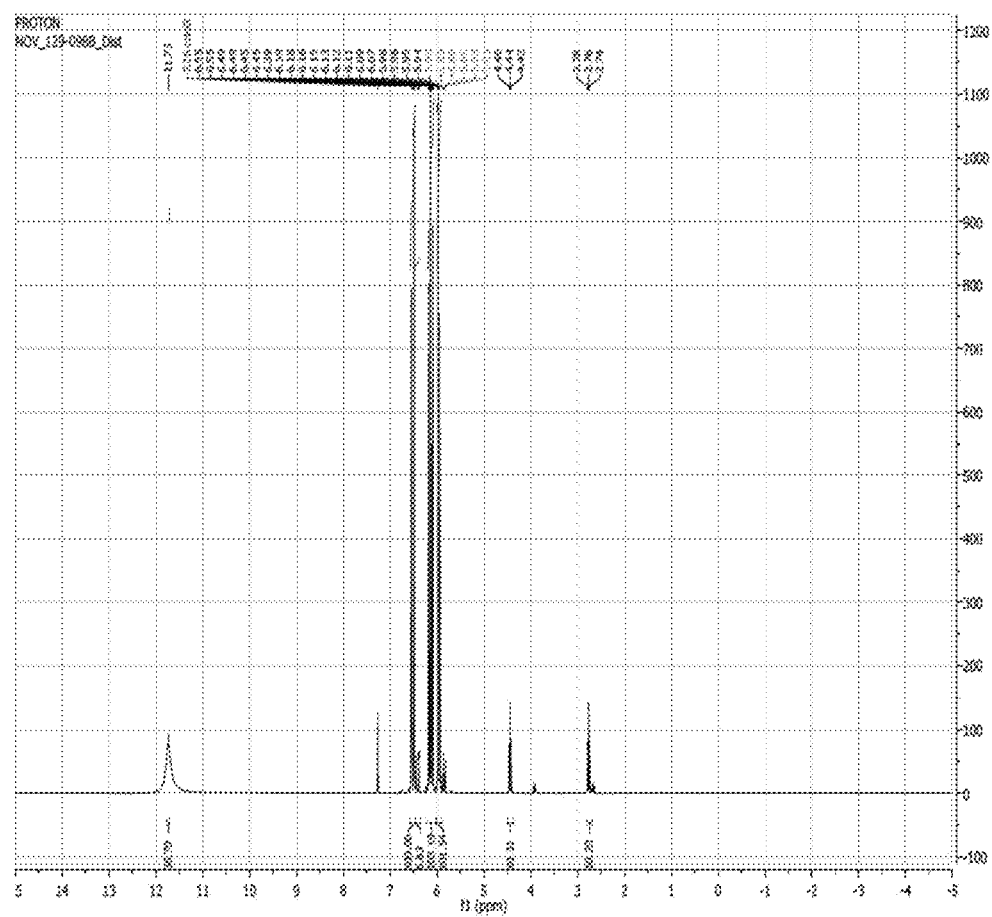
FIG. 6 illustrates a H NMR graph of a product stream from a preferred embodiment maintaining a concentration of active salt between 1% and 5% by weight.

FIG. 6 illustrates the hydrogen nuclear magnetic resonance graph of an acrylic acid product stream from an embodiment of the present invention wherein the process included maintaining a concentration range of sodium acrylate between 1% and 5% by weight in the thermolysis process vessel.

The acrylic acid product represented by the FIG. 6 illustration is produced using a lab-scale batch thermolysis process vessel comprising a two-necked round-bottom glass flask of 25 mL approximate internal volume. The thermolysis process vessel is equipped with an internal thermocouple and the top center opening of the thermolysis process vessel includes a separation chamber comprising a short-path distillation apparatus including a short path still (similar to Ace Glass item #6554-06) with an additional thermocouple to monitor vapor temperature, followed by a water-cooled condenser, and finally a four-armed product receiver in a dry ice/acetone-cooled dewar. The thermolysis process vessel includes a heater comprising a fabric heating mantle, the power to which is controlled by a temperature controller that receives feedback from the thermocouple inside the thermolysis process vessel. The thermolysis process vessel includes a stirrer comprising a magnetic stir plate and a PTFE-coated stir bar.

The feed stream introduced to the thermolysis process vessel comprises 90 mg dry sodium acrylate, 5 mg phenothiazine, and 4.995 g of PPL produced from ring-opening polymerization of solvent-free bPL in the presence of sodium acrylate at a concentration of 1 mol per 6,000 mol of bPL and phenothiazine at a concentration of 200 ppmw in bPL. The feed stream in the thermolysis process vessel is heated to 90° C. to melt and begin stirring. The thermolysis process vessel is brought under vacuum to an absolute pressure of approximately 700 torr, and the thermolysis process vessel temperature setpoint is set to 210° C. Internal reflux is observed inside the thermolysis process vessel within minutes and the thermolysis process vessel is held at 210° C. for 10 minutes.

The total product collected weighed 4.7816 g. The product sample 129-098B_Dist HNMR analysis suggests an average acrylic acid content in 129-098B_Dist of 90.7% by mass. The balance consists of di-acrylic acid ester and traces of other PPL oligomers where n>2.

Figure 7:
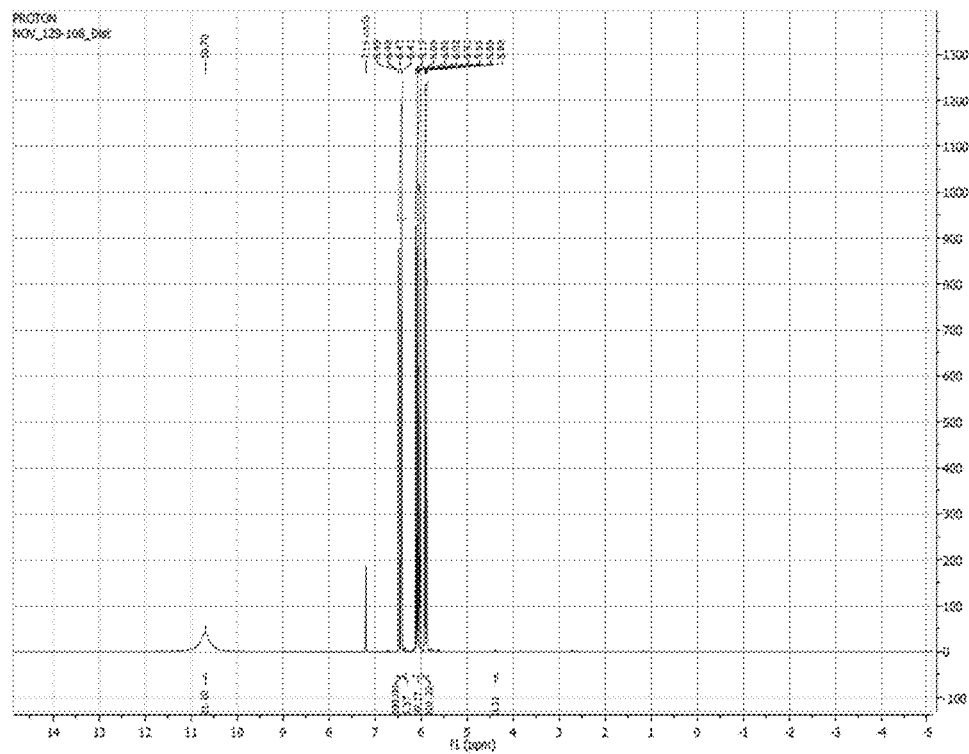
FIG. 7 illustrates a H NMR graph of a product stream from a preferred embodiment maintaining a concentration of active salt between 5% and 10% by weight.

FIG. 7 illustrates the hydrogen nuclear magnetic resonance graph of an acrylic acid product stream from an embodiment of the present invention wherein the process included maintaining a concentration range of sodium acrylate between 5% and 10% by weight in the thermolysis process vessel.

The acrylic acid product represented by the FIG. 7 illustration was produced using a lab-scale batch thermolysis process vessel comprising a two-necked round-bottom glass flask of 50 mL approximate internal volume. The thermolysis process vessel includes an internal thermocouple and a separation chamber located at the top center opening in the thermolysis process vessel. The separation chamber comprises a distillation apparatus including two Vigreux columns in series oriented coaxially (each similar to Ace Glass item #6578-04), followed by an adapter with an additional thermocouple to monitor vapor temperature, followed by a water-cooled condenser, and finally a 50 mL round-bottom product receiver in a dry ice/acetone-cooled dewar. The thermolysis process vessel includes a heater comprising a fabric heating mantle, the power to which is controlled by a temperature controller that receives feedback from the thermocouple inside the thermolysis process vessel. The thermolysis process vessel includes a stirrer comprising a magnetic stir plate and a PTFE-coated stir bar.

The feed stream introduced to the thermolysis process vessel comprises 1000 mg dry sodium acrylate, 20 mg phenothiazine, and 19.162 g of PPL produced from ring-opening polymerization of solvent-free bPL in the presence of sodium acrylate at a concentration of 1 mol per 6,000 mol of bPL and phenothiazine at a concentration of 200 ppmw in bPL. The feed stream in the thermolysis process vessel is heated to 90° C. to melt and begin stirring. The thermolysis process vessel is brought under vacuum to an absolute pressure of approximately 90 torr, and the thermolysis process vessel temperature setpoint is set to 165° C. Internal reflux is observed inside the thermolysis process vessel within minutes. The thermolysis process vessel is held at 165° C. for 40 minutes.

The product sample 129-108_Dist had a weight of 14.659 g and consisted of all the distillate collected. Residual material in the reaction flask weighed 4.7186 g. HNMR analysis suggests an average acrylic acid content in 129-108_Dist of 99.7%. The balance consists of di-acrylic acid ester and traces of other PPL oligomers where n>2.

The embodiments described herein are not intended to be limited to the aspects shown, but are to be accorded the widest scope consistent with the principles and features disclosed herein.

What is claimed is:

1. A process for producing acrylic acid from a feed stream containing polypropiolactone, the process comprising:
    a. passing the feed stream to a decomposition chamber of a thermolysis process vessel;
    b. maintaining an active salt comprising sodium acrylate in the decomposition chamber of the thermolysis vessel at a predetermined concentration range wherein a portion of the active salt is removed from the decomposition chamber;
    c. contacting the feed stream with the active salt in the decomposition chamber at thermolysis conditions and converting at least a part of the feed stream to acrylic acid;
    d. withdrawing a product stream comprising acrylic acid; and
    e. recovering at least a portion of the acrylic acid from the product stream wherein the decomposition chamber has an active salt concentration in the range of 0.02 to 10 wt %.

2. The process of claim 1 wherein the feed stream has a polypropiolactone concentration of at least 95 wt %.

3. The process of claim 1 wherein the feed stream has beta-propiolactone concentration of less than 2 wt %.

4. The process of claim 1 wherein the product stream is withdrawn in a vapor phase.

5. The process of claim 1 wherein the active salt is at a concentration in the decomposition chamber in the range of 1 to 5 wt %.

6. The process of claim 5 wherein the feed stream is a liquid and contains the active salt at a concentration in a range of 0.01 to 1 wt %.

7. The process of claim 5 wherein a purge stream comprising active salt is withdrawn from the decomposition chamber at a rate that is adjusted relative to the withdrawal rate of the product stream and input rate of the feed stream to maintain the sodium acrylate concentration in the decomposition chamber within a predetermined range.

8. The process of claim 1 wherein at least one heater directly contacts the feed stream in the decomposition chamber to supply heat to the feed stream contained therein.

9. The process of claim 4 wherein the product stream in vapor phase flows directly from the decomposition chamber into a separation chamber in direct communication with the decomposition chamber for separating acrylic acid from lower boiling materials.

10. The process of claim 1 wherein the decomposition chamber is maintained at a pressure in a range of 1 torr and 5,000 torr and a temperature in range of 100° C. and 300° C.

11. The process of claim 1 wherein the feed stream enters the decomposition chamber and the product stream leaves the decomposition chamber at an average residence time in a range of 1 minute to 24 hours.

12. The process of claim 1 wherein the product stream comprises acrylic acid having a concentration in a range of 90% and 99.8% by weight.

13. The process of claim 1 wherein at least a portion of the feed stream is heated prior to entering the decomposition chamber to supply heat to the decomposition vessel.

\* \* \* \* \*